US006244865B1

United States Patent
Nelson et al.

(10) Patent No.: US 6,244,865 B1
(45) Date of Patent: Jun. 12, 2001

(54) TONGUE POSITIONING DEVICE WITH OPTIONAL FILTER

(75) Inventors: Dale Nelson, Corona; Michael J. Salemi, Alameda, both of CA (US)

(73) Assignee: Sensormedics Corporation, Yorba Linda, CA (US)

( * ) Notice: Subject to any disclaimer, the term of this patent is extended or adjusted under 35 U.S.C. 154(b) by 0 days.

(21) Appl. No.: 09/454,832

(22) Filed: Dec. 6, 1999

(51) Int. Cl.$^7$ ........................................ A61F 5/56
(52) U.S. Cl. .................. 433/140; 128/860; 128/205.29; 600/239
(58) Field of Search ............................ 433/140; 128/848, 128/859, 860, 863, 205.29; 600/237, 238, 239, 240

(56) References Cited

U.S. PATENT DOCUMENTS

| | | | |
|---|---|---|---|
| 307,930 | * | 11/1884 | Ehrhardt . |
| 2,669,988 | * | 2/1954 | Carpenter . |
| 4,148,308 | * | 4/1979 | Sayer . |
| 4,425,911 | * | 1/1984 | Luomanen et al. . |
| 4,495,945 | * | 1/1985 | Liegner . |
| 5,024,218 | * | 6/1991 | Ovassapian et al. . |
| 5,086,768 | * | 2/1992 | Niemeyer ........................ 128/205.29 |
| 5,465,734 | * | 11/1995 | Alverez et al. ........................ 128/848 |
| 5,533,523 | * | 7/1996 | Bass, Jr. et al. ........................ 128/859 |
| 5,590,643 | * | 1/1997 | Flam ........................ 128/859 |
| 5,782,234 | * | 7/1998 | Bates ........................ 128/205.29 |
| 5,868,138 | | 2/1999 | Halstrom ........................ 128/848 |
| 5,915,385 | * | 6/1999 | Hakimi ........................ 128/848 |
| 6,010,458 | * | 1/2000 | Roberts ........................ 128/205.29 |

* cited by examiner

Primary Examiner—Ralph A. Lewis
(74) Attorney, Agent, or Firm—Lyon & Lyon LLP

(57) ABSTRACT

A tongue positioning device is disclosed for positioning the tongue within a user's mouth. The device includes a tongue positioning mouthpiece that includes a mouthpiece body with a center hole therein. A flange portion extends around the periphery of the mouthpiece body that forms an acoustic seal with the teeth and lips of a patient during use. A pair of bite blocks protrude from the mouthpiece body on opposing lateral sides of the center hole. A tongue bridge is fixedly secured to the bite blocks via a pair of downwardly extending arms. The tongue bridge includes a platform area where a patient's tongue is placed under when the mouthpiece is used. A cylindrical portion extends from the mouthpiece body in a direction away from the flange. An optional filter is removable from the cylindrical portion and acts as a protective barrier for viruses, bacteria, microbes, and other pathogens. The filter includes a removable filter body containing a filter media. The tongue bridge can also be incorporated into an oral appliance.

43 Claims, 4 Drawing Sheets

TONGUE POSITIONING DEVICE WITH OPTIONAL FILTER

BACKGROUND OF THE INVENTION

The field of the invention relates generally to oral devices. More specifically, the invention relates to mouthpieces and oral appliances for use in clinical, diagnostic, and imaging tests for the study, diagnosis, and treatment of breathing disorders. The invention can also be used in conjunction with devices that measure pulmonary function such as spirometry-type devices. The invention may also be used with airway resistance measurement devices. The device may also be used in connection with other imaging techniques for the upper airway region.

Sleep related breathing disorders (SBD's) adversely affect the breathing of individuals during periods of sleep. Breathing disruption in sleep often results from the collapse or closing of an individual's air passageway. Sleep apnea, as one common example of a SBD, is an abnormal physical condition that affects a person's ability to breath properly after falling asleep. Persons suffering from sleep apnea can stop breathing for periods as short as a few seconds and as long as a few minutes.

Typically, SBD's such as sleep apnea are treated by Continuous Positive Air Pressure (CPAP) therapy. In CPAP therapy, a device that is essentially an air pump forces air into an individuals air passageway. The CPAP device maintains sufficient pressure to keep the air passageway open during periods of sleep. The patient typically wears a mask-like device that is connected to the CPAP device to provide the elevated air pressure into the upper air passageway. Other devices known as BiPAP (Bi-Level Positive Airway Pressure) devices operate at two positive air pressure levels. A lower pressure level is used during patient exhalation while a higher pressure level is used during inhalation. The BiPAP devices make it easier to exhale due to the lower pressure used during exhalation. BiPAP devices are often proscribed for individuals that require higher pressures than those present in CPAP devices.

For many individuals that suffer from a SBD, CPAP and BiPAP therapy are not appropriate. A significant portion of these individuals, however, may be treated successfully with oral appliances. An oral appliance is a device that is positioned with a patient's mouth to correct the diagnosed problem or condition. One example of an oral appliance is the intra-oral appliance described in U.S. Pat. No. 5,868,138 issued to Halstrom. U.S. Pat. No. 5,868,138 is incorporated by reference as if set forth fully herein. The device may, for example, alter the position of the patient's jaw to open-up the patient's airway.

When using oral appliances, it is necessary to determine the efficacy of such appliances through the use of diagnostic tests or studies. In this regard, the appropriate type of appliance for a particular patient can be chosen. In addition, the optimal characteristics of an individual oral appliance is readily obtainable. Typically, the diagnostic studies or tests measure the cross-sectional area (CSA) in the pharynx region of the patient. These tests permit clinicians to determine the effect of the oral appliance on the CSA. One technique that measures CSA includes acoustic pharyngometry (AR).

Unfortunately, there are several limitations to the accuracy and repeatability of these tests in measuring CSA. First, the position of the tongue can significantly impact CSA readings in the upper airway. Proper tongue placement is critical for upper airway assessments because the base of the tongue defines the anterior wall of the oropharynx. Minor movements of the tongue can significantly skew the CSA data, making diagnosis difficult.

Separate and apart from the tests that measure CSA, there are still other pulmonary tests and diagnostic methods that require proper placement of the tongue and jaw. Spirometry, for example, is one pulmonary test that can be adversely effected by improper placement of the tongue or jaw. Like the tests that measure CSA, improper placement of the tongue and/or jaw can adversely effect the accuracy and repeatability of these other tests.

In the case of acoustic pharyngometry, medical technologists are charged with the task of coaching patients on proper tongue placement. Because it is impossible to directly observe the position of the tongue in the patient's mouth, the medical technologist must instruct the patient to move their tongue into the proper position (ideally, down and forward in the mouth). The medical technologist must then interpret the data to determine whether the patient has, in fact, achieved proper tongue placement. The technologist generally looks for artifacts that are created in the test results. This, however, is problematic because artifacts are difficult to identify. Moreover, there is no standard or baseline that is consistent across different individuals because the size and structure of the mouth varies between individuals. This further complicates the job of the medical technologist.

As with the tongue, the position of the jaw can also affect the CSA. Different jaw positions can create artifacts in the test results.

Accordingly, there is a need for a device that permits an individual to stabilize the placement of the tongue during diagnostic examination. The device preferably permits accuracy and repeatability in clinical, diagnostic, and imaging tests by stabilizing movement of both the tongue and jaw. The device would further permit the insertion of imaging probes and diagnostic devices into the oral cavity while the device is in place. In this regard, the efficacy of the oral appliance would be accurately measured without being adversely impacted by artifacts.

In addition to being used in diagnostic examinations, the tongue positioning mechanism can also be used in the actual oral appliances that are used by a patient. In this regard the oral appliance gives optimal placement of the tongue within the oral cavity.

Moreover, the device, when used as a mouthpiece, preferably can include an optional filter that would eliminate the need to disinfect testing or diagnostic devices between patient uses.

SUMMARY OF THE INVENTION

In a first aspect of the present invention, a tongue positioning mouthpiece is disclosed. The tongue positioning mouthpiece includes a mouthpiece body that has a center hole therein. A flange is located around the periphery of the mouthpiece body. A pair of bite blocks protrude from the mouthpiece body such that the bite blocks are located on opposing lateral sides of the center hole. A tongue bridge is fixedly secured to the mouthpiece. The tongue bridge is located below the centerline of the center hole and away from the mouthpiece body. The tongue bridge further includes a platform where a patient's tongue is placed under during use of the mouthpiece.

In a second aspect of the present invention, a tongue positioning mouthpiece according to the first aspect further includes a pair of downwardly extending arms originating at the bite blocks and extending downward, terminating below the centerline of the center hole and away from the mouthpiece body. A tongue bridge is fixedly secured between the terminating ends of the downwardly extending arms.

In a third aspect of the present invention, a tongue positioning mouthpiece according to the second aspect further includes a cylindrical portion extending in a direction away from the flange. The cylindrical portion further includes a hollow passageway connecting to the center hole.

In a fourth aspect of the present invention, a tongue positioning mouthpiece according to the second aspect further includes an abutment located on the interior surface of the cylindrical portion. A front flexible o-ring seal is fixedly attached thereon and extends away from the abutment to form a gap between the front flexible o-ring seal and the interior surface of the cylindrical portion. The mouthpiece also includes a removable filter body having a retaining ring therein, an air-tight seal formed between the filter body and the mouthpiece body when the filter body is inserted into the mouthpiece body. A filter media is sandwiched between the front flexible o-ring seal and the retaining ring. The filter media acts as a protective barrier for viruses, bacteria, microbes, and other pathogens.

In another aspect of the invention, a tongue positioning device for fixing the placement of the tongue within a user's mouth is disclosed. The device includes upper and lower bite block elements covering the user's teeth. A tongue bridge is fixedly secured to either the upper or lower bite block elements. The tongue bridge includes a tongue platform under which the user places his or her tongue during use.

DETAILED DESCRIPTION OF THE PREFERRED EMBODIMENT

Figure 1:
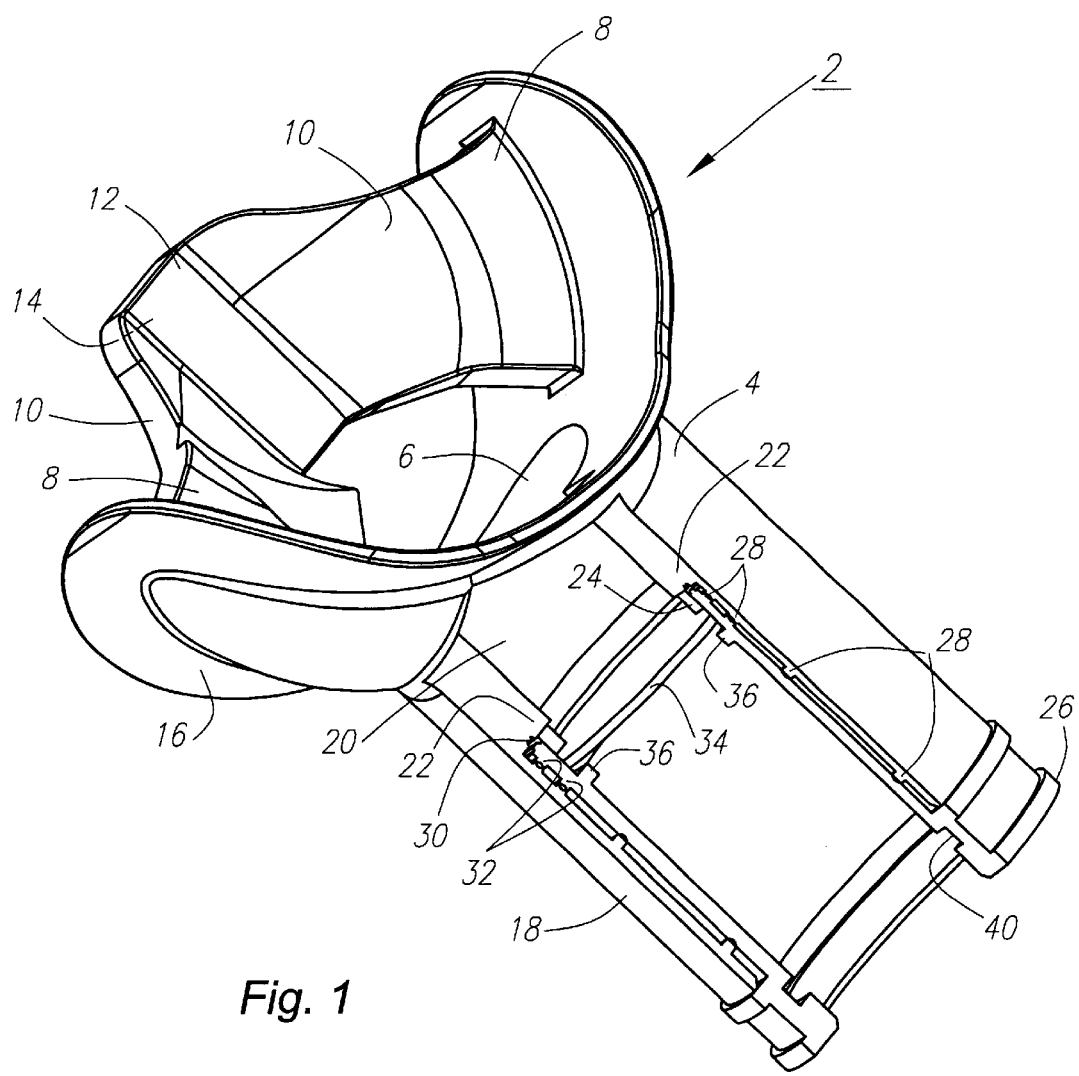
FIG. 1 is a perspective view of the tongue positioning mouthpiece with a cut-away section removed from the mouthpiece body.
Figure 2:
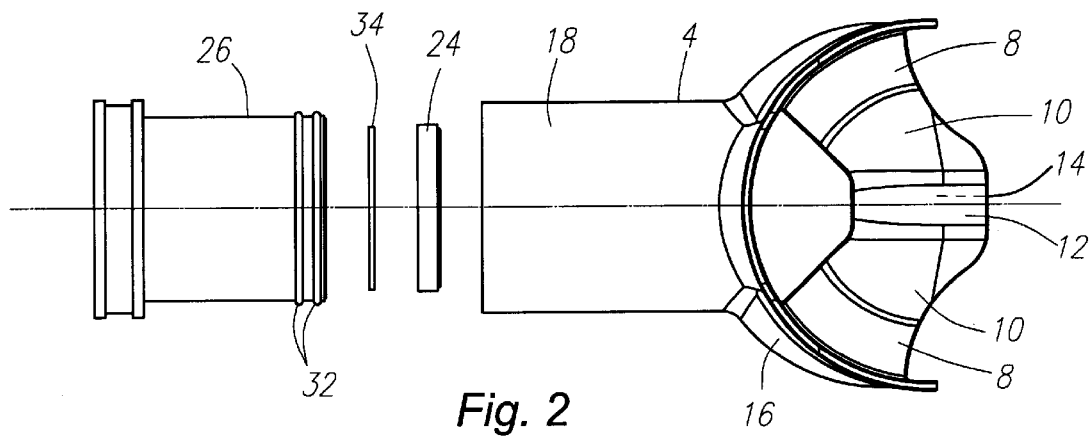
FIG. 2 is an assembly view of the tongue positioning mouthpiece showing the mouthpiece body, the front flexible o-ring seal, filter media, and filter body.
Figure 3:
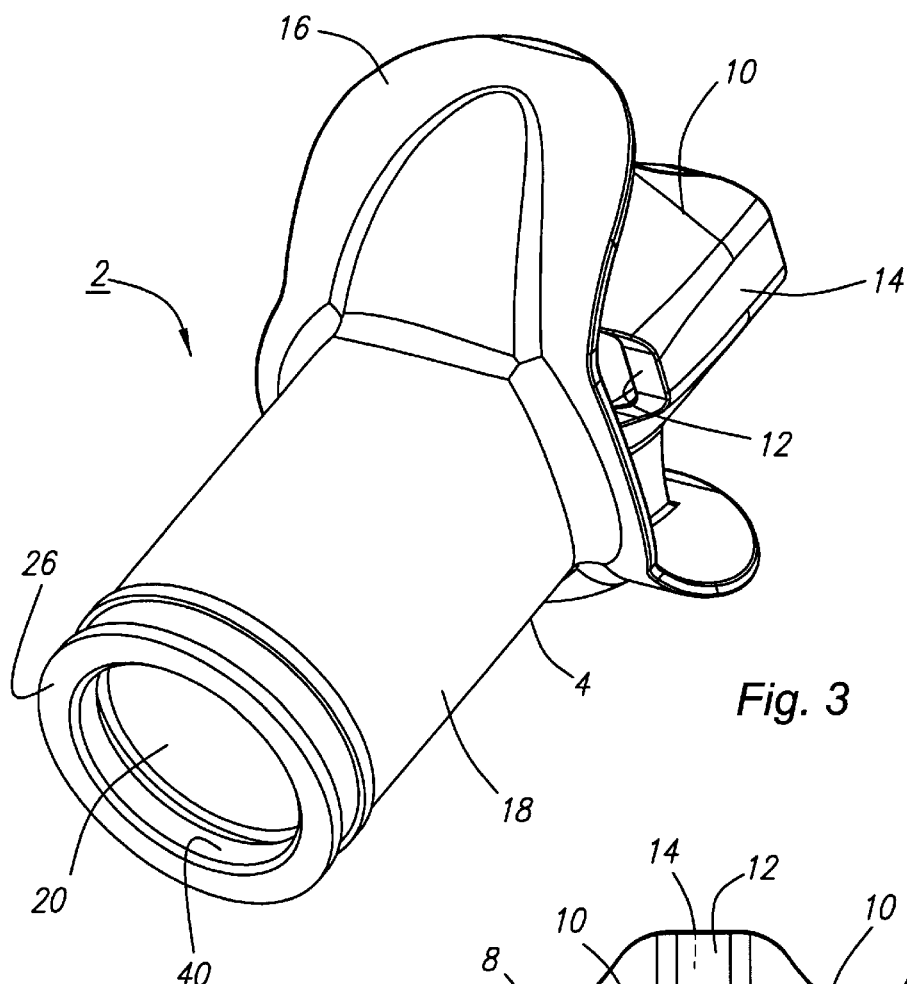
FIG. 3 is another perspective view of the tongue positioning mouthpiece.
Figure 4:
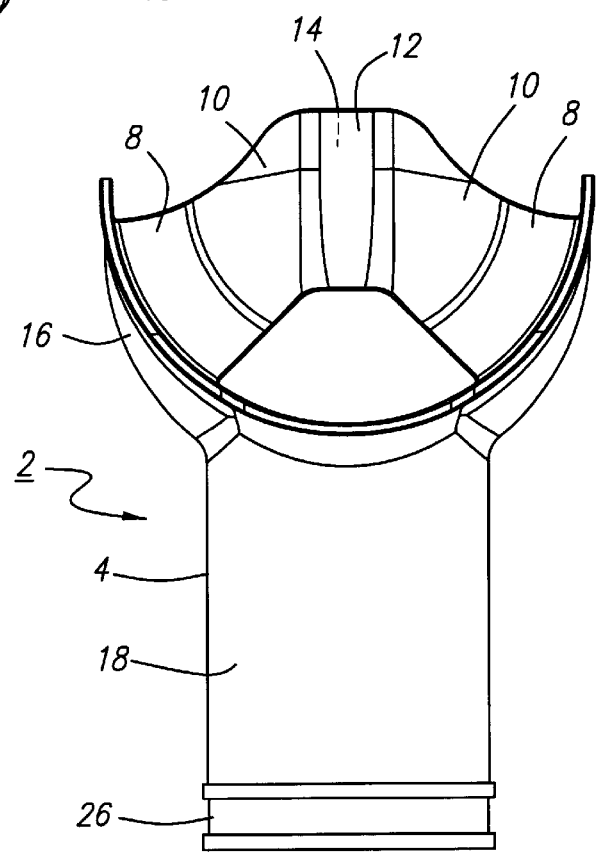
FIG. 4 is a top-view of the tongue positioning mouthpiece.
Figure 5:
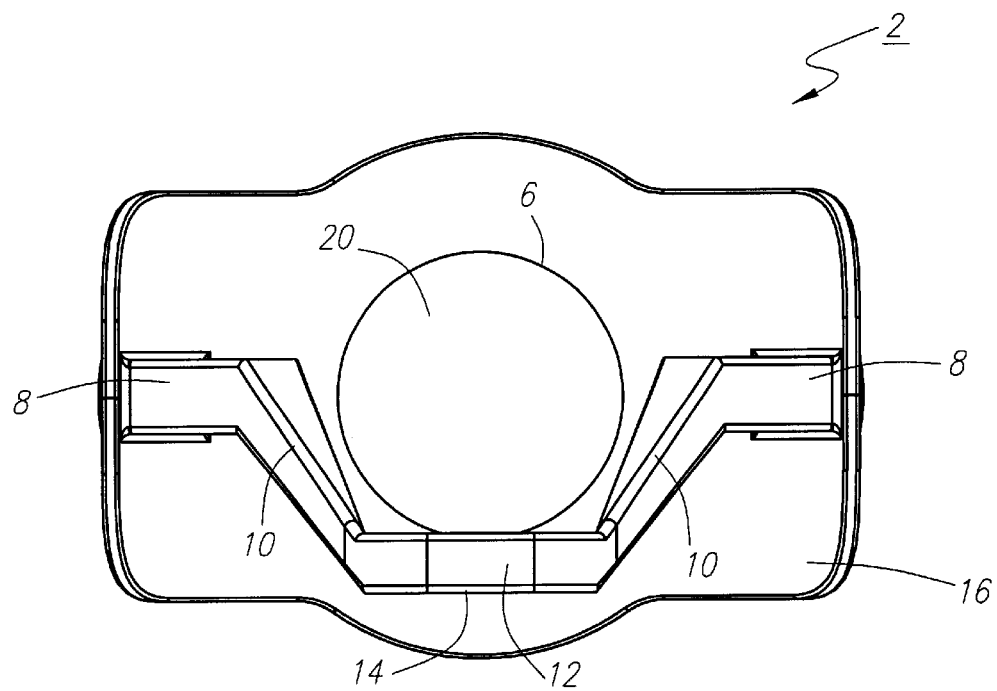
FIG. 5 is a frontal view of the tongue positioning mouthpiece.
Figure 6:
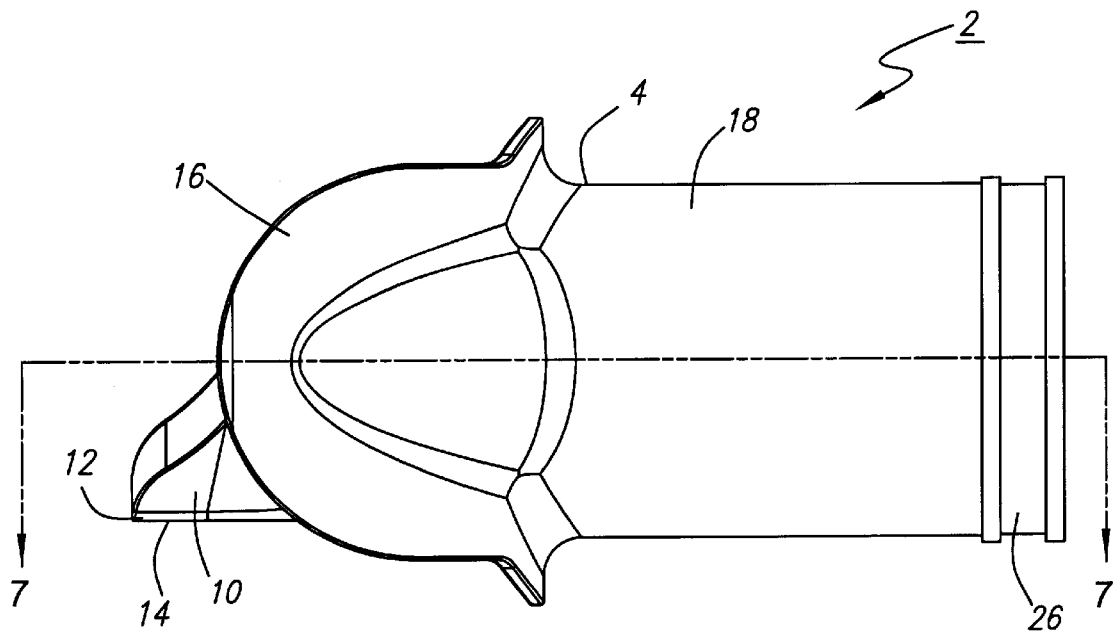
FIG. 6 is a side view of the tongue positioning mouthpiece.

Turning now to the drawings, FIGS. 1–8 show several views of the tongue positioning mouthpiece 2. The tongue positioning mouthpiece 2 has a mouthpiece body 4. The mouthpiece body 4 includes a center hole 6 therein. The tongue positioning mouthpiece 2 can be made out of any number of materials, including injection-molded, blow-molded, thermal-set, and compression-molded plastic. It is contemplated that virtually any solid material that can be cleaned, disinfected, or autoclaved could be used. One preferred example of such a material is a thermoplastic rubber, SANTOPRENE 8000 Series, available from Advanced Elastomer Systems, L.P., 388 S. Main Street, Akron, Ohio 44311. Referring to FIGS. 1, 2, 4, 5, and 7, the tongue positioning mouthpiece 2 preferably includes a pair of bite blocks 8 that protrude away from the surface of the mouthpiece body 4. The bite blocks 8 are positioned on laterally opposing sides of the center hole 6 in the mouthpiece body 4. During use of the tongue positioning mouthpiece 2, a user clenches the bite blocks 8 between his or her teeth (upper and lower dental arches). The bite blocks 8 serve to lock the jaw of the user in place during clinical, diagnostic, and imaging studies. In addition, the bite blocks 8 also open the jaw slightly to allow probes, tools, sound waves, diagnostic devices, and other devices to pass between the teeth and into the oral cavity when the mouthpiece is used in conjunction with devices that utilize probes and tools, and the like.

Located on the same side of the tongue positioning mouthpiece 2 as the bite blocks 8 is a tongue bridge 12. The tongue bridge 12 is preferably flat and includes a platform surface 14. During use, a patient positions his or her tongue under the platform surface 14 of the tongue bridge 12. The tongue bridge 12 thus regulates and fixes the location of the tongue in a predetermined location. Fixing the tongue under the tongue bridge 12 permits repeatability in clinical, diagnostic, and imaging studies. The tongue bridge 12 allows the tongue to be optimally positioned in the down and forward position in the mouth.

As recited below in greater detail, the tongue bridge 12 may also be used in connection with an oral appliance to position the tongue. In this manner, the tongue bridge 12 may be employed in a variety of tongue positioning devices, including, for example, mouthpieces and oral appliances.

The tongue bridge 12 is preferably located below the centerline of the center hole 6 and is away from the surface of the mouthpiece body 4. The term away is meant to indicate that the tongue bridge 12 is displaced at a distance from the surface of the mouthpiece body 4. As can be seen in FIGS. 1, 2, 4, and 6, the tongue bridge 12 preferably extends beyond the terminal end portions of the flange 16. In this manner, the tongue bridge 12 is positioned deeper within the oral cavity to better keep the tongue in the down and forward position. The tongue bridge 12 may be secured to the tongue positioning mouthpiece 2 by direct attachment to the mouthpiece body 4, via the bite blocks 8, or through downwardly extending arms 10.

Preferably, the tongue bridge 12 is fixedly secured to the bite blocks 8 via a pair of downwardly extending arms 10. The downwardly extending arms 10 are fixedly attached to the pair of bite blocks 8. The downwardly extending arms 10 both extend downward and away from the surface of the mouthpiece body 4. In this regard, the downwardly extending arms 10 terminate at a location that is below the centerline of the center hole 6 and is away from the surface of the mouthpiece body 4.

Preferably, the tongue bridge 12 (and platform surface 14), the downwardly extending arms 10, and the bite blocks 8 are constructed of the same material as the mouthpiece body 4. However, other materials may be used. The tongue bridge 12, downwardly extending arms 10, and the bite blocks 8 can be integrally formed into the mouthpiece body 4, or alternatively, formed separately and joined to the mouthpiece body 4. The tongue bridge 12, downwardly extending arms 10, and the bite blocks 8 may also be strengthened by adding different types of plastic materials or support structures. For example, a plastic insert may be overmolded during mouthpiece formation to increase the overall strength and stability of the tongue positioning mouthpiece 2.

The tongue bridge 12 and the bite blocks 8 act in conjunction with one another to minimize movements of the jaw and stabilize the tongue. At the same time, the tongue positioning mouthpiece 2 provides access for the insertion of probes, diagnostic devices, and the like into the oral cavity so the appropriate test can be performed when used with devices where such insertion occurs.

Located on the side of the mouthpiece body 4 opposite the tongue bridge 12 is the cylindrical portion 18 of the mouthpiece body 4. The cylindrical portion 18 is contiguous with the mouthpiece body 4 and is preferably formed as an extension of the mouthpiece body 4. As seen in FIGS. 1, 3, 5, 7, and 8, the cylindrical portion 18 of the mouthpiece body 4 has a hollow passageway 20 therein. The hollow passageway 20 connects to the center hole 6 located within the mouthpiece body 4. In this manner, a conduit is formed such that air can pass freely into and out of the patients mouth during inhalation and expiration. In addition, the hollow passageway 20 permits probes, diagnostic devices and the like to be freely passed in and out of the patient's mouth. Depending on the diagnostic test that is performed, the terminal end of the cylindrical portion 18 of the mouthpiece body is connected to a diagnostic device or is opened to the atmosphere. Probes and the like may be passed into and through the hollow passageway 20 depending on the type and nature of the diagnostic test.

In one preferred embodiment of the invention, the hollow passageway 20 of the mouthpiece body includes an abutment 22. The abutment 22 is preferably a continuous ring about the inside of the mouthpiece body 4 that projects radially inward toward the centerline of the center hole 6. Also according to this preferred embodiment, a front flexible o-ring seal 24 fixedly secured to the abutment 22. Preferably, the front flexible o-ring seal 24 is directly molded into the abutment 22. The front flexible o-ring seal 24 is located at the junction between the abutment 22 and a filter body 26 described hereinafter.

Figure 7:
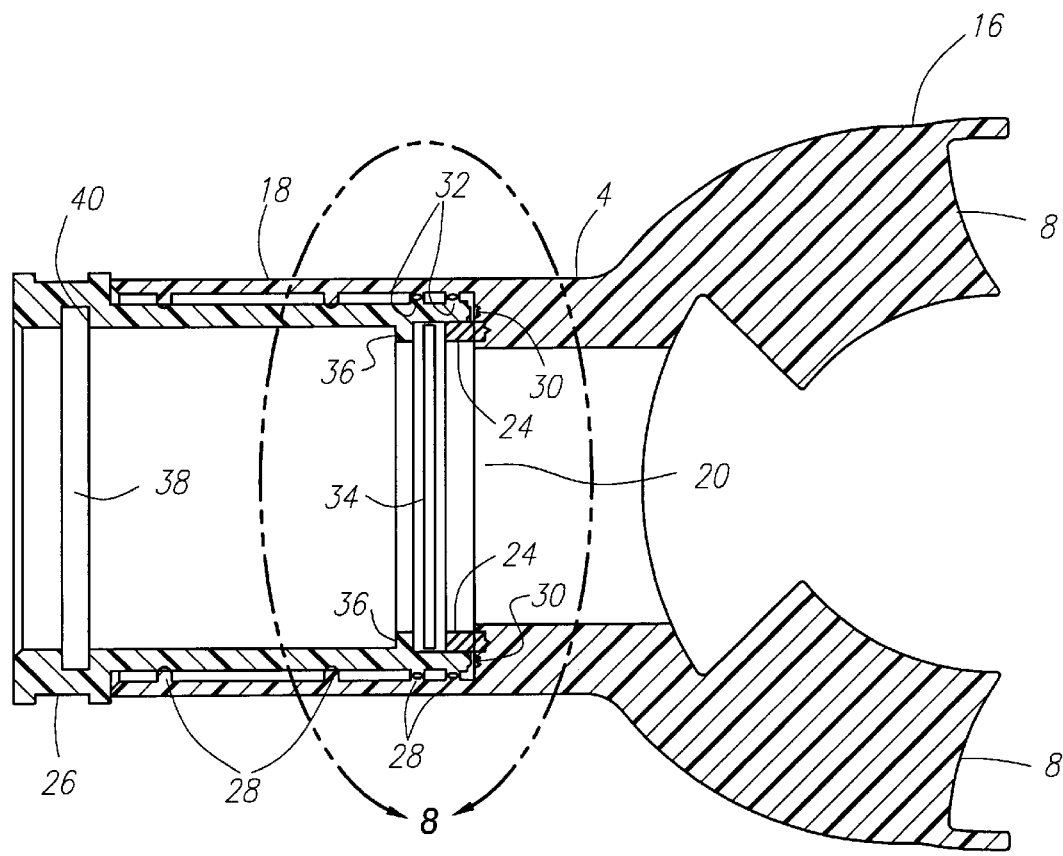
FIG. 7 is plan view taken along the line 7—7 of FIG. 6.
Figure 8:
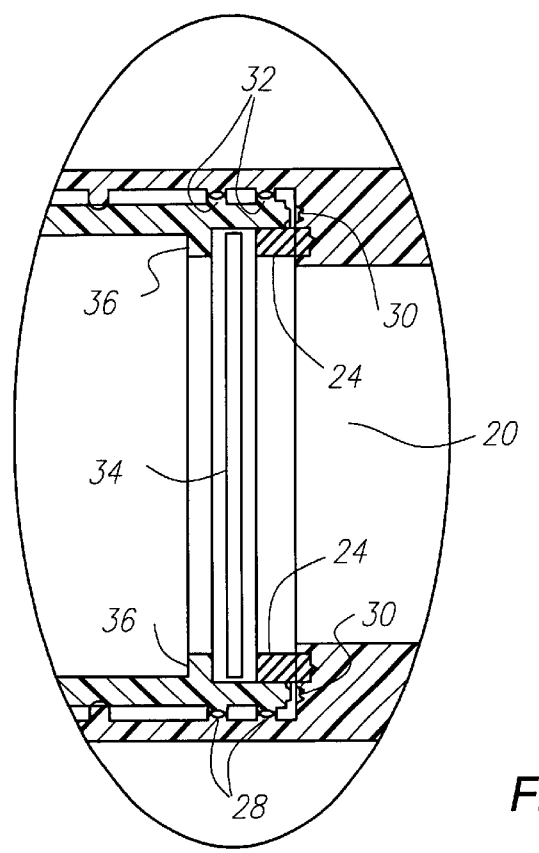
FIG. 8 is a close-up view of region 8 shown in FIG. 7.

Also located on the inner wall of the hollow passageway 20 of the mouthpiece body 4 are a plurality of molded rings 28. The molded rings 28 act to hold into position as well as seal the filter body 26 in the mouthpiece body 4. The molded rings 28 are preferably integrally molded into the mouthpiece body 4. As seen in FIGS. 1 and 7, four separate molded rings 28 are shown. The molded rings 28 project radially inward toward the center line of the center hole 6. The molded rings 28, however, do not extend past the outer periphery of the front flexible o-ring seal 24. In this regard, a gap 30 is produced between the outermost extension of the molded rings 28 and the outer periphery of the front flexible o-ring seal 24. This gap 30 is the location of where the filter body 26 is inserted into the mouthpiece body 4. Preferably, the two forward-most (toward the front flexible o-ring seal 24) molded rings 28 are somewhat shorter in height than the rearward molded rings 28. This is done because the filter body 26 preferably includes corresponding flexible circumferential nubs 32 that engage and lock with the forward-most molded rings 28.

When the tongue positioning mouthpiece 2 is used by a patient, the patient bites down on bite blocks 8. In this regard, the flange 16 covers the mouth area of the patient, while the cylindrical portion 18 extends and projects outward from the patient's mouth.

Referring to FIGS. 1, 2, 7, and 8, the tongue positioning mouthpiece 2 optionally includes a filter media 34 located inside the filter body 26. The filter media 34 acts as a barrier for viruses, bacteria, and other pathogens. In this manner, the filter media 34 in its associated filter body 26 create an air-tight seal between the patient and the corresponding instrument or device. By using the filter media 34 in connection with the mouthpiece 2, there is no need to disinfect, between patient uses, any instruments, diagnostic devices or the like that are connected to the tongue positioning mouthpiece 2.

Associated with the filter media 34 is the filter body 26. The filter body 26 has a hollow center and is preferably made of an injectable, thermal-set, compression molded, or machinable plastic material. The filter body 26 not only serves as a support piece for the filter media 34, it also adds strength and stability to the mouthpiece body 4. The filter body 26 inserts into the cylindrical portion 18 of the mouthpiece body 4. As stated above, the filter body 26 inserts into the gap 30 created between the front flexible o-ring seal 24 and the molded rings 28. Except for the contact points described herein, the outer diameter of the filter body 26 is less than the inner diameter of the hollow passageway 20.

The air-tight seal is created by inserting the filter body 26 into the hollow passageway 20 of the mouthpiece body 4. The filter body 26 is pressed toward the front of the mouthpiece body 4 until the filter body 26 frictionally engages with at least one of the foreword-most molded rings 28. The filter body 26 is then pushed further inside the mouthpiece body 4 with additional force until the front edge of the filter body 26 contacts the front flexible o-ring seal 24 and the abutment 22. At this point, the front section of the filter body 26 is sandwiched in the gap 30 between the front flexible o-ring seal 24 and the forward-most molded rings 28. In addition, flexible circumferential nubs 32 present on the exterior surface of the filter body 26 engage with the forward-most molded rings 28 to create a locking engagement of the filter body 26 inside the mouthpiece body 4. Moreover, additional molded rings 28 are located to the rear of the filter body 26. These additional molded rings 28 further aid in supporting and sealing the filter body 26 within the mouthpiece body 4.

Referring now to FIGS. 1, 2, 7, and 8, sandwiched between the front flexible o-ring seal 24 and the filter body 26 lies the filter media 34. The filter media 34 is held in place by a retaining ring 36 on the filter body 26 that extends radially inward toward the center line of the center hole 6. The retaining ring 36 provides a press-fit locking mechanism for securing the filter media 34. The retaining ring 36 preferably has a raised section along the contact surface that embeds into the filter media 34 to aid in creating an air-tight seal and retaining the filter media 34.

The filter body 26 also incorporates a rear flexible o-ring seal 38, similar to the front flexible o-ring seal 24, that lies within a rear groove 40 of the filter body 26. This rear flexible o-ring seal 38 acts to form an air-tight seal between the tongue positioning mouthpiece 2/filter body 26 and the mating diagnostic device or instrument. In addition, the rear flexible o-ring seal 38 also acts as a retainer that engages with, for example, a tube of the diagnostic instrument or device. As one illustrative example, the metal tube of a pharyngometer fits within the opening of the filter body 26 and engages the rear flexible o-ring seal 38 in a mating engagement.

It should be appreciated that the internal shape of the filter body 26 can be modified depending on the type of device that the tongue positioning mouthpiece 2 connects with. The shape, as well as the internal size of the opening of the filter body 26 changes depending on the particular nature of the attached device.

In addition, the invention further contemplates using the tongue positioning mouthpiece 2 in conjunction with a conventional-type filter. In this embodiment, the filter media 34 is not used. Instead, a conventional bacterial/viral filter, such as the MICROGUARD filter distributed by Sensor-Medics Corporation, 22705 Savi Ranch Parkway, Yorba Linda, Calif. 92887-4645, may be used. In this embodiment, the tongue positioning mouthpiece 2 may use a filter body 26 as an interface piece to engage with the conventional-type filter. In this construction, the filter body 26 does not include any filter media 34. Alternatively, the mouthpiece body 4 may directly attach to the conventional-type filter in a press-fit engagement, without any filter body 26. In another embodiment, the tongue positioning mouthpiece 2 may be integrally formed onto a conventional-type filter with the mouthpiece body 4 being continuous with the conventional-type filter.

The filter media 34 can be made of any number of materials capable of substantially eliminating the pass-through of bacteria, viruses, and other microbes from the patient's mouth and into the diagnostic instrument. Preferably, the filter media 34 is made of an electrostatic-type microbial filter.

Located on the periphery of the mouthpiece body 4 is a flange 16. The flange 16 preferably creates an acoustic seal between the lips and the teeth of a patient, when the mouthpiece 2 is positioned inside a patient's mouth. The acoustic seal is needed for studies where acoustic reflection techniques are employed.

As stated previously, the tongue positioning mouthpiece 2 serves to stabilize the jaw and tongue during diagnosis and imaging studies. The tongue positioning mouthpiece 2 can be used with, for purposes of illustration and not by way of limitation, acoustic pharyngometry, magnetic resonance imaging (MRI), computer tomography (CAT), fluoroscopy, lung scans, impulse oscillometry, spirometry, and airway resistance measurements. The tongue positioning mouthpiece 2 can be used with many devices that measure, diagnose, or treat pulmonary conditions. The tongue positioning mouthpiece 2 can be used with, for example, the following clinical procedures: (1) assessing risk for a SBD by determining the CSA of sites in the upper airway; (2) determining the efficacy of an oral appliance for the treatment of a SBD, by determining the appliances effect on the CSA; (3) pre-intubation assessments; (4) pre-surgical assessments; (5) vocal cord dysfunction assessments; (6) general otorhinolaryngology (ear, nose, and throat) evaluations; (7) reducing or eliminating obstructions during impulse oscillometry studies; and (8) avoiding particle rain-out of inhaled aerosols during radiographic and non-radiographic lung scans.

In yet another aspect of the invention, it is contemplated that the tongue bridge 12 forms a part of the actual oral appliance used by a patient. In this embodiment, the tongue bridge 12 is optimally positioned to keep the patient's tongue in the desired position within the mouth. Preferably, the tongue would be positioned down and forward in the patient's mouth when using the oral appliance. The tongue bridge 12 preferably includes a platform surface 14 under which, the tongue is placed. Preferably, the tongue bridge 12 is connected to either of the lower or upper bite blocks of the oral appliance. Most preferably, the tongue bridge 12 connects to the lower bite block of the oral appliance. The tongue bridge 12 can attach directly to the bite blocks of the oral appliance, or indirectly via arms 10, like those used in the mouthpiece embodiment.

When the tongue bridge 12 is used in the oral appliance, a separate mouthpiece body 4 without any tongue bridge 12 or bite blocks 8 can be used for diagnostic purposes. In this regard, the mouthpiece is a scaled-down version of the tongue positioning mouthpiece 2 described above. The mouthpiece would still, however, include a mouthpiece body 4 and flange portion 16. The flange 16 creates an acoustic seal between the lips and teeth of a user when the mouthpiece is worn. Diagnostic imaging and studies can thus be performed when the oral appliance is in place. Of course, the scaled-down mouthpiece can optionally include a separable filter body 26 with filter media 34 as described above in greater detail.

While embodiments of the present invention have been shown and described, various modifications may be made without departing from the scope of the present invention, and all such modifications and equivalents are intended to be covered.

What is claimed is:

1. A tongue positioning mouthpiece comprising:

a mouthpiece body including a center hole therein, the body further including a flange portion around the periphery thereof;

a pair of bite blocks protruding from the mouthpiece body, the bite blocks positioned on opposing lateral sides of the center hole; and a tongue bridge fixedly secured between the pair of bite blocks, the tongue bridge located below the centerline of the center hole and disposed away from the mouthpiece body, the tongue bridge further including a platform where a patient's tongue is placed under during use of the mouthpiece.

2. A tongue positioning mouthpiece according to claim 1, wherein the flange creates an acoustic seal between the lips and teeth of a patient when used.

3. A tongue positioning mouthpiece according to claim 1, the mouthpiece body further including a cylindrical portion extending in a direction away from the flange, the cylindrical portion further including a hollow passageway therein that connects to the center hole.

4. A tongue positioning mouthpiece according to claim 3, wherein the mouthpiece body includes an abutment on an interior surface of the cylindrical portion having a front flexible o-ring seal fixedly attached thereon.

5. A tongue positioning mouthpiece according to claim 4, further including a removable filter body positionable within the hollow passageway of the cylindrical portion between the front flexible o-ring seal and the interior of the cylindrical portion.

6. A tongue positioning mouthpiece according to claim 5 further including a plurality of molded rings on the interior surface of the cylindrical portion of the tongue positioning mouthpiece, said plurality of molded rings frictionally engaging with the filter body.

7. A tongue positioning mouthpiece according to claim 6, the filter body further including means for holding a filter media.

8. A tongue positioning mouthpiece according to claim 7, the front flexible o-ring seal forming an air-tight seal between the mouthpiece body and the filter body.

9. A tongue positioning mouthpiece according to claim 3, the mouthpiece body including a filter media within the cylindrical portion of the mouthpiece body.

10. tongue positioning mouthpiece according to claim 9, wherein the filter media is removable from the mouthpiece body.

11. A tongue positioning mouthpiece according to claim 3, the cylindrical portion connecting to a filter.

12. A tongue positioning mouthpiece comprising:
a mouthpiece body including a center hole therein, the body further including a flange portion around the periphery thereof;
a pair of bite blocks protruding from the mouthpiece body, the bite blocks positioned on opposing lateral sides of the center hole;
a pair of downwardly extending arms originating at the pair of bite blocks and extending down and terminating below the centerline of the center hole and away from the surface of the mouthpiece body; and
a tongue bridge fixedly secured to the pair of downwardly extending arms at their point of termination, the tongue bridge located below the centerline of the center hole and away from the mouthpiece body, the tongue bridge further including a platform where a patient's tongue is placed under during use of the mouthpiece.

13. A tongue positioning mouthpiece according to claim 12, wherein the flange creates an acoustic seal between the lips and teeth of a patient when used.

14. A tongue positioning mouthpiece according to claim 12, the mouthpiece body further including a cylindrical portion extending in a direction away from the flange, the cylindrical portion further including a hollow passageway therein that connects to the center hole.

15. A tongue positioning mouthpiece according to claim 14, the mouthpiece body including a filter media within the cylindrical portion of the mouthpiece body.

16. tongue positioning mouthpiece according to claim 15, wherein the filter media is removable from the mouthpiece body.

17. A tongue positioning mouthpiece according to claim 14, wherein the mouthpiece body includes an abutment on an interior surface of the cylindrical portion having a front flexible o-ring seal fixedly attached thereon.

18. A tongue positioning mouthpiece according to claim 17, further including a removable filter body positionable within the hollow passageway of the cylindrical portion between the front flexible o-ring seal and the interior of the cylindrical portion.

19. A tongue positioning mouthpiece according to claim 18, further including a plurality of molded rings on the interior surface of the cylindrical portion of the tongue positioning mouthpiece, said plurality of molded rings frictionally engaging with the filter body.

20. A tongue positioning mouthpiece according to claim 19, the filter body further including means for holding a filter media.

21. A tongue positioning mouthpiece according to claim 20, the front flexible o-ring seal forming an air-tight seal between the mouthpiece body and the filter body.

22. A tongue positioning mouthpiece comprising:
a mouthpiece body including a center hole therein, the body further including a flange portion around the periphery thereof;
a pair of bite blocks protruding from the mouthpiece body, the bite blocks positioned on opposing lateral sides of the center hole;
a pair of downwardly extending arms originating at the pair of bite blocks and extending down and terminating below the centerline of the center hole and away from the surface of the mouthpiece body;
a tongue bridge fixedly secured between the pair of bite blocks, the tongue bridge located below the centerline of the center hole and away from the mouthpiece body; and
a cylindrical portion extending in a direction away from the flange, the cylindrical portion further including a hollow passageway connecting to the center hole.

23. A tongue positioning mouthpiece according to claim 22, the tongue bridge having a tongue platform, wherein a patient's tongue is placed beneath while using the tongue positioning mouthpiece.

24. A tongue positioning mouthpiece according to claim 22, wherein the flange creates an acoustic seal between the lips and teeth of a patient when used.

25. A tongue positioning mouthpiece according to claim 22, the mouthpiece body including a filter media within the cylindrical portion of the mouthpiece body.

26. A tongue positioning mouthpiece according to claim 25, wherein the filter media is removable from the mouthpiece body.

27. A tongue positioning mouthpiece according to claim 22, wherein the mouthpiece body includes an abutment on an interior surface of the cylindrical portion having a front flexible o-ring seal fixedly attached thereon.

28. A tongue positioning mouthpiece according to claim 27, further including a removable filter body positionable within the hollow passageway of the cylindrical portion between the front flexible o-ring seal and the interior of the cylindrical portion.

29. A tongue positioning mouthpiece according to claim 28, further including a plurality of molded rings on the interior surface side of the cylindrical portion of the tongue positioning mouthpiece, said plurality of molded rings frictionally engaging with the filter body.

30. A tongue positioning mouthpiece according to claim 29, the filter body further including means for holding a filter media.

31. A tongue positioning mouthpiece according to claim 29, the front flexible o-ring seal forming an air-tight seal between the mouthpiece body and the filter body.

32. A tongue positioning mouthpiece according to claim 22, the cylindrical portion connecting to a filter.

33. A tongue positioning mouthpiece comprising:
mouthpiece body including a center hole therein, the body further including a flange portion around the periphery thereof;
a pair of bite blocks protruding from the mouthpiece body, the bite blocks positioned on opposing lateral sides of the center hole;
a pair of downwardly extending arms originating at the pair of bite blocks and extending down and terminating below the centerline of the center hole and away from the surface of the mouthpiece body;
a tongue bridge fixedly secured to the pair of downwardly extending arms at their point of termination, the tongue bridge located below the centerline of the center hole and away from the mouthpiece body, the tongue bridge further including a platform where a patient's tongue is placed under during use of the mouthpiece;
a cylindrical portion extending in a direction away from the flange, the cylindrical portion further including a hollow passageway connecting to the center hole, the cylindrical portion of the mouthpiece body further including an abutment on the interior surface thereof, the abutment further including a front flexible o-ring seal fixedly attached thereon, the front flexible o-ring seal extending away from the abutment to form a gap region between the front flexible o-ring seal and the interior cylindrical portion;
a removable filter body having a retaining ring therein, an air-tight seal formed between the removable filter body and the mouthpiece body when the removable filter body is positioned in the mouthpiece body; and a filter media that acts as a protective barrier for viruses, bacteria, microbes, and other pathogens, the filter media sandwiched between the front flexible o-ring seal and the retaining ring of the filter body.

34. A tongue positioning mouthpiece according to claim 33, the filter media being removable from the removable filter body.

35. A tongue positioning mouthpiece according to claim 34, further including a plurality of molded rings on the interior surface of the cylindrical portion of the tongue positioning mouthpiece, said plurality of molded rings frictionally engaging with the removable filter body.

36. A tongue positioning mouthpiece according to claim 35, the removable filter body further including a plurality of circumferential nubs that engage with the molded rings on the interior surface of the cylindrical portion of the tongue positioning mouthpiece.

37. A tongue positioning mouthpiece comprising:

a mouthpiece body including a center hole therein, the body including a flange portion around the periphery thereof, the body further including a cylindrical portion extending in a direction away from the flange, the cylindrical portion including a hollow passageway therein that connects to the center hole;

a filter media disposed within the cylindrical portion of the mouthpiece body;

a pair of bite blocks protruding from the mouthpiece body, the bite blocks positioned on opposing lateral sides of the center hole; and a tongue bridge fixedly secured to the mouthpiece, the tongue bridge located below the centerline of the center hole and away from the mouthpiece body, the tongue bridge further including a platform where a patient's tongue is placed under during use of the mouthpiece.

38. A tongue positioning mouthpiece according to claim 37, wherein the filter media is removable from the mouthpiece body.

39. A tongue positioning mouthpiece comprising:

a mouthpiece body including a center hole therein, the body including a flange portion around the periphery thereof, the body further including a cylindrical portion extending in a direction away from the flange, the cylindrical portion including a hollow passageway therein that connects to the center hole;

an abutment located on an interior surface of the cylindrical portion of the mouthpiece body, the abutment having a front flexible o-ring seal fixedly attached thereon;

a pair of bite blocks protruding from the mouthpiece body, the bite blocks positioned on opposing lateral sides of the center hole; and a tongue bridge fixedly secured to the mouthpiece, the tongue bridge located below the centerline of the center hole and away from the mouthpiece body, the tongue bridge further including a platform where a patient's tongue is placed under during use of the mouthpiece.

40. A tongue positioning mouthpiece according to claim 39, further including a removable filter body positionable within the hollow passageway of the cylindrical portion between the front flexible o-ring seal and the interior of the cylindrical portion.

41. A tongue positioning mouthpiece according to claim 40, further including a plurality of molded rings on the interior surface of the cylindrical portion of the tongue positioning mouthpiece, said plurality of molded rings frictionally engaging with the filter body.

42. A tongue positioning mouthpiece according to claim 41, the filter body including means for holding a filter media.

43. A tongue positioning mouthpiece according to claim 42, the front flexible o-ring seal forming an air-tight seal between the mouthpiece body and the filter body.

* * * * *

UNITED STATES PATENT AND TRADEMARK OFFICE
CERTIFICATE OF CORRECTION

PATENT NO. : 6,244,865 B1
DATED : June 12, 2001
INVENTOR(S) : Nelson et al.

It is certified that error appears in the above-identified patent and that said Letters Patent is hereby corrected as shown below:

Column 5,
Line 15, change "patients" to -- patient's --.
Line 31, change "seal 24 fixedly" to -- seal 24 is fixedly --.

Column 8,
Line 63, change "tongue" to -- A tongue --.

Column 10,
Line 39, change "mouthpiece" to -- a mouthpiece --.

Signed and Sealed this

Twenty-first Day of May, 2002

JAMES E. ROGAN
Director of the United States Patent and Trademark Office

Attest:

Attesting Officer